United States Patent
Punsch et al.

(10) Patent No.: US 10,463,602 B2
(45) Date of Patent: Nov. 5, 2019

(54) AQUEOUS HAIR STYLING COMPOSITION COMPRISING HIGH AMOUNTS OF WAXES AND FATTY COMPOUNDS

(71) Applicant: KAO GERMANY GMBH, Darmstadt (DE)

(72) Inventors: Britta Punsch, Darmstadt (DE); Sabine Schmid, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 15/277,471

(22) Filed: Sep. 27, 2016

(65) Prior Publication Data
US 2018/0028435 A1  Feb. 1, 2018

(30) Foreign Application Priority Data
Jul. 26, 2016 (EP) .................................. 16181295

(51) Int. Cl.
| | |
|---|---|
| *A61K 8/92* | (2006.01) |
| *A61K 8/55* | (2006.01) |
| *A61K 8/81* | (2006.01) |
| *A61K 8/39* | (2006.01) |
| *A61K 8/36* | (2006.01) |
| *A61K 8/06* | (2006.01) |
| *A61K 8/37* | (2006.01) |
| *A61K 8/31* | (2006.01) |
| *A61K 8/34* | (2006.01) |
| *A61K 8/84* | (2006.01) |
| *A61Q 5/06* | (2006.01) |

(52) U.S. Cl.
CPC .............. *A61K 8/922* (2013.01); *A61K 8/062* (2013.01); *A61K 8/31* (2013.01); *A61K 8/342* (2013.01); *A61K 8/361* (2013.01); *A61K 8/37* (2013.01); *A61K 8/375* (2013.01); *A61K 8/39* (2013.01); *A61K 8/55* (2013.01); *A61K 8/8176* (2013.01); *A61K 8/8182* (2013.01); *A61K 8/84* (2013.01); *A61K 8/92* (2013.01); *A61K 8/927* (2013.01); *A61Q 5/06* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,536,519 A | 8/1985 | Suzuki et al. | |
| 5,582,832 A * | 12/1996 | Pillai | A61K 8/4946 424/401 |
| 2007/0166258 A1* | 7/2007 | Pratley | A61K 8/0295 424/70.7 |
| 2007/0202068 A1* | 8/2007 | Walter | A61K 8/86 424/70.12 |
| 2007/0248550 A1* | 10/2007 | Patel | A61K 8/19 424/59 |
| 2007/0265209 A1 | 11/2007 | Goget et al. | |
| 2011/0135589 A1* | 6/2011 | Knappe | A61K 8/8182 424/70.12 |
| 2013/0056017 A1* | 3/2013 | Rigsby | A45D 20/12 132/271 |
| 2014/0262867 A1* | 9/2014 | Weinberg | A45D 34/00 206/229 |

FOREIGN PATENT DOCUMENTS

| | | |
|---|---|---|
| DE | 10 2008 040 102 A1 | 1/2010 |
| EP | 1792607 A1 | 6/2007 |
| EP | 1792640 A1 | 6/2007 |
| EP | 1800647 A1 | 6/2007 |

OTHER PUBLICATIONS

Cremer Care, "Softisan® 649", pp. 1-5 (2013).*

* cited by examiner

*Primary Examiner* — Bethany P Barham
*Assistant Examiner* — Barbara S Frazier
(74) *Attorney, Agent, or Firm* — Norris McLaughlin, P.A.

(57) ABSTRACT

The present invention relates to a hair styling composition with high amount of waxes and fatty compounds, use, and kit-of-parts thereof. It has been found out that a composition comprising one or more fatty substances, one or more wax components, one or more specific anionic surfactants and one or more styling polymers provides satisfactory styling effect on coarse hair and has satisfactory storage stability.

15 Claims, No Drawings

AQUEOUS HAIR STYLING COMPOSITION COMPRISING HIGH AMOUNTS OF WAXES AND FATTY COMPOUNDS

BACKGROUND OF THE INVENTION

The present invention relates to a hair styling composition with high amount of waxes and fatty compounds, use, and kit-of-parts thereof.

Many customers have coarse hair resulting either from their genetic disposition or from chemical and mechanical stress on hair fibers. Chemical stress factors such as bleaching, coloring, perming and/or straightening are known to damage the hair thereby leading to coarse hair surfaces and a subsequent change of the inner hair structure. Once the hair is progressively damaged, it is prone to breakage under relatively low mechanical forces. Furthermore, coarse hair is very often stubborn and difficult to shape and style. Best known approaches for styling of very coarse hair are treating the hair with highly viscous products such as pastes, pomades, and hair waxes.

Compositions with high fat and/or wax content for styling hair are known from EP1792640 and DE102008040102. They make use of various surfactants but do not achieve long-term stability. Compositions without styling polymers comprising high amount of fats and/or waxes are disclosed in U.S. Pat. No. 4,536,519, EP1800647, and EP1792607, and do not confer the amount of hold needed for coarse hair.

Compositions comprising high contents of fatty substances and/or waxes (e.g. more than 30% by weight, calculated to the total of the composition) form emulsions which tend to separate in two phases and, therefore, lack long-term storage stability.

Moreover, these kinds of compositions can reach quite high viscosities and are, therefore, difficult to apply and to distribute on the hair. Irrespective of the product's viscosity, it is generally more difficult to distribute styling products on coarse hair.

SUMMARY OF THE INVENTION

Therefore, the present invention aims at providing a styling composition for coarse hair, which allows easy application and distribution of the composition on the hair and at the same time, has satisfactory storage stability. None of the prior art documents attempt to solve these problems.

The inventors of the present invention have unexpectedly found out that a composition comprising one or more fatty substances, one or more wax components, one or more specific anionic surfactant(s) and one or more styling polymer(s) provides satisfactory styling effect on coarse hair and has satisfactory storage stability.

Thus, the first object of the present invention is an aqueous composition for styling hair characterized in that it comprises
a) one or more fatty substance(s),
b) one or more waxes at a concentration of equal to or more than 20% by weight, calculated to the total of the composition,
c) one or more anionic surfactants and/or their salts according to the general structure

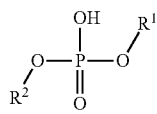

wherein $R^1$ is a linear alkyl chain with $C_6$ to $C_{22}$, and $R^2$ is selected from H or linear alkyl chain with $C_6$ to $C_{12}$ with the provision that if $R^2$ is H then $R^1$ is selected from $C_{12}$ to $C_{22}$,
d) one or more styling polymers.

The second object is the use of the composition to temporarily change the texture and/or shape of the hair.

The third object is a kit-of-parts comprising the composition of the present invention and a shampoo and/or a blow dryer.

DETAILED DESCRIPTION OF THE INVENTION

The term 'wax' within the meaning of the present invention is a lipophilic compound whose majority is solid at 20° C. This includes compounds which start to melt below 20° C., but which are completely molten at a temperature 20° C. and above.

Suitable waxes are beeswax, lanolin wax, carnauba wax, candelilla wax, ouricury wax, rice bran wax, berry wax, shellac wax, orange wax and lemon wax, microcrystalline waxes, petrolatum-based products such as Petroleum jelly, as well as their mixtures. Further suitable waxes are diesters of adipic acid with mixed diesters of caprylic, capric, hydroxystearic, and isostearic acid which are available under the CTFA names bis-diglyceryl polyacyladipate-1 and bis-diglyceryl polyacyladipate-2, as well as their mixtures.

In principle wax fatty esters can be selected by their melting point above 20° C. Special reference is made to the publication from Marosi and Schlenk (Liebigs Ann. Chem 1973, 584-598) who published melting points for a great series of fatty acid esters. Suitable wax fatty esters are for example octyl stearate, myristyl myristate, cetyl palmitate, octyl palimitate, and lauryl palmitate.

Suitable wax fatty alcohols are the ones with a carbon chain length of 14 to 30 C atoms which may be saturated or unsaturated, linear or branched which may as well be substituted. Non-limiting examples are cetyl alcohol, stearyl alcohol and their mixture known as cetearyl alcohol.

Suitable wax fatty acids are the ones with a carbon chain length of 14 to 30 C atoms which may be saturated and linear, and may as well be substituted. Non-limiting examples are lauric acid, myristic acid, palmitic acid, stearic acid, behenic acid, as well as their mixtures.

Suitable wax petrolatum-based products are linear and/or branched paraffins with a carbon chain length of $C_6$ to $C_{12}$. A non-limiting example is petroleum jelly.

The preferred waxes are bis-diglyceryl polyacyladipate-1 and bis-diglyceryl polyacyladipate-2.

The composition of the present invention may comprise waxes at a total concentration ranging from 20% to 60% by weight, preferably from 20% to 50% by weight, and more preferably from 25% to 45% by weight, calculated to the total of the composition.

Fatty substances within the meaning of the present invention are lipophilic compounds which have a melting point below 20° C. and are liquid at 20° C.

Suitable fatty substances are non-wax $C_{10}$- to $C_{36}$-fatty acid triglycerides, non-wax fatty alcohols, or non-esterified, non-wax fatty acids, non-wax esterified fatty alcohols and acids, as well as non-wax petrolatum-based products.

Suitable $C_{10}$- to $C_{36}$-fatty acid triglycerides are selected from vegetable origin. Vegetable $C_{10}$- to $C_{36}$-fatty acid triglycerides are for example castor oil, coconut oil, corn oil, cottonseed oil, olive oil, palm kernel oil, peanut oil, rapeseed oil, sunflower oil, safflower oil, sesame oil, soybean oil, almond oil, cashew oil, hazelnut oil, jojoba oil, macadamia oil, pecan oil, pine nut oil, pistachio oil, walnut oil, grapefruit seed oil, lemon oil, orange oil, pumpkin seed oil, flaxseed oil, apricot kernel oil, argan oil, avocado oil, babassu oil, grape seed oil, mustard oil, poppyseed oil, prune kernel oil, rice bran oil, and wheat germ oil.

Suitable non-wax fatty alcohols are the ones liquid at room temperature and with a carbon chain length of 14 to 30 C atoms which are predominatly unsaturated and branched fatty alcohols which may as well be substituted. Non-limiting examples are oleyl alcohol, 2-octyldodecyl alcohol, isostearyl alcohol, as well as their mixtures.

Suitable non-wax fatty acids are the ones with a carbon chain length of 14 to 30 C atoms which may be saturated or unsaturated, linear or branched which may as well be substituted. Non-limiting examples are ricinoleic acid, caprylic acid, oleic acid, and linoleic acid, as well as their mixtures.

In principle non-wax fatty esters can be selected by their melting point below 20° C. Special reference is made to the publication by Marosi and Schlenk (Liebigs Ann. Chem 1973, 584-598) who published melting points for a great series of fatty acid esters. A suitable non-wax fatty ester is for example isopropyl palmitate.

Suitable non-wax petrolatum-based products are linear and/or branched paraffins with a carbon chain length of C6 to C12, mineral oils and preferably light mineral oils.

The non-wax fatty substance is preferably selected from light mineral oils.

The total concentration of fatty substances is in the range from 1% to 25%, preferably 5% to 20% by weight, and more from 5% to 15% by weight, calculated to the total of each composition.

The weight ratio of total waxes to total fatty substances is in the range from 0.1 to 10, 0.1 to 8, preferably from 0.1 to 5, more preferably from 0.1 to 3.

The composition is an oil in water emulsion and comprises one or more anionic surfactants of the general structure below.

Suitable anionic surfactants and/or their salts according to the general structure

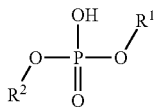

wherein $R^1$ is a linear alkyl chain with $C_6$ to $C_{22}$, and $R^2$ is selected from H or linear alkyl chain with $C_6$ to $C_{12}$ with the provision that if $R^2$ is H then $R^1$ is selected from $C_{12}$ to $C_{22}$, Suitable anionic surfactants and/or their salts wherein $R^2$ is H according to the structure above are dodecyl phosphate, tridecyl phosphate, tetradecyl phosphate, pentadecyl phosphate, hexadecyl phosphate, heptadecyl phosphate, octadecyl phosphate, nonadecyl phosphate, eicosyl phosphate, heneicosanyl phosphate, and docosanoic phosphate, as well as their mixtures.

Further suitable anionic surfactants and/or their salts with $R^2$ is not H according to the structure from above are dihexyl phosphate, diheptyl phosphate, dioctyl phosphate, dinonyl phosphate, dodecyl phosphate, and diundecyl phosphate, as well as their mixtures.

The preferred anionic alkyl phosphate surfactant is cetyl phosphate and/or its salts such as lithium, sodium, potassium, magnesium, calcium, or ammonia. The most preferred salt is the potassium salt.

The total concentration of anionic surfactants and/or their salts according to the present invention is in the range from 0.1% to 10%, preferably from 0.2% to 7.5%, and more preferably from 0.25% to 5%, most preferably from 0.25% to 2.5% by weight, calculated to the total of the composition.

Styling polymers according to the present invention are selected from anionic, cationic, amphoteric, or non-ionic polymers. Preferably it is a non-ionic styling polymer.

As amphoteric polymers which can be used alone or in mixture with at least one additional non-ionic polymer, reference is here made in particular to copolymers of N-octyl acrylamide, (meth)acrylic acid and tert.-butyl-aminoethyl-methacrylate of the type "Ampho-mer®"; copolymers from methacryloyl ethyl betaine and alkyl meth-acrylates of the type "Yuka-former®", e.g. the butyl-methacrylate copolymer "Yukaformer® Am75"; copolymers from monomers containing carboxyl groups and sulfonic groups, e.g., (meth) acrylic acid and itaconic acid, with monomers such as mono- or dialkyl aminoalkyl (meth)acrylates or mono- or dialkyl aminoalkyl (meth)-acrylamides containing basic groups, in particular amino groups; c¬ opolymers from N-octylacrylamide, methyl methacrylate, hydroxypropyl methacrylate, N-tert.-butyl aminoethy methacrylate and acrylic acid, as well as the copolymers known from U.S. Pat. No. 3,927,199.

Suitable anionic polymers in combination with non-ionic polymers are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g., "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof.

Further suitable anionic polymers are acrylate copolymers available under trade name Salcare SC 81, PEG/PPG 25/25 dimethicone/acrylate copolymer available under trade name Luviflex Silk from BASF, Acrylates/t-butylacrylamide copolymer available under trade name Ultrahold Strong, Advantage LC-E which is vinylcaprolactam/PVP/dimethyl-aminoethylmethacrylate copolymer and VA/crotonates copolymer available under trade name Luviset CA 66.

The composition of the present invention may comprise, although less preferred, cationic polymers in combination with non-ionic polymer. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 24, Polyquaternium 67, and Polyquaternium 72.

The term non-ionic means that the polymer does not carry a permanent charge in its bulk stage.

More preferably the non-ionic styling polymer is a homopolymer of vinylpyrrolidone. BASF Corporation offers such polymers under the trade names Luviskol K for purchase.

Natural non-ionic polymers are as well suitable for the composition of the present invention. Those are such as cellulose, chitosan, guar gum, neutralised shellac and their derivatives.

Typical molecular weight ranges for polyvinylpyrrolidones suitable for the present invention range from 10 kDa up to 200 kDa, preferably from 20 kDa to 100 kDa, more preferably from 30 kDa to 90 kDa, wherein the molecular weight ranges are given as average molecular weight ranges.

The composition may further comprise copolymers as non-ionic styling polymers. Suitable copolymers comprise units of vinylpyrrolidone and at least one more co-monomer selected from vinylacetate, styrene, vinylpyridine, and vinylimidazole. Preferably the composition comprises a poly-(vinylpyrrolidone-co-vinylacetate) copolymer wherein the ratio of comonomers can be varied ranging from VP/VA 30:70 to VP/VA 70:30. Such polymers have a typical average molecular weight ranging from 20 kDa to 40 kDa and are offered for sale by BASF Corporation under the trade name Luviskol VA.

The total concentration of styling polymers in the compositions is from 1% to 20%, more preferably from 1% to 15%, and more preferably from 2% to 10% by weight, calculated to the total of the composition.

The composition may further comprise one or more nonionic surfactants, preferably ester or ether of ethylene oxide and fatty acids or fatty alcohols. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, poly-condensates of ethyleneoxide and propyleneoxide, as they are on the market, for example, under the trade name "Pluronics®". Suitable non-ionic surfactants are esters or ethers of ethylene oxide and fatty acids or fatty alcohols, such as ethoxylated castor oil, ethoxylated coconut fatty acid, ethoxylated lauric acid, ethoxylated oleic acid, ethocylated stearic acid, sorbitan esters, such as polyethylene glycol sorbitan stearic, palmitic, myristic and lauric acid esters, fatty acid polyglycol esters or, as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

The concentration of one or more non-ionic surfactant in the composition is to be selected according to the concentration of the anionic surfactant. The weight ratio of total anionic to total non-ionic surfactant is from 0.1 to 20, preferably from 1 to 15, and more preferably from 1 to 10.

The composition may further comprise silicones for example linear polysiloxanes such as dimethicones with various consistency and dimethiconols, aminated silicones with primary, secondary, tertiary or quaternary ammonium groups such as amodimethicone, polysilicone 9, polysilicone-28 and quaternium 80, cyclic silicones such as cyclomethicones, arylated silicones such as phenyl trimethicone. Total concentration of silicone compounds is in the range from 0.1% to 20% by weight, preferably from 1% to 15% by weight, and more preferably from 2% to 10% by weight, calculated to the total of the composition.

The composition may further comprise one or more ceramide compound, such as the one according to general formula

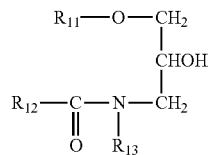

where $R_{11}$ and $R_{12}$ are independent from each other alkyl- or. Alkenyl group with 10 to 22 carbon atoms, $R_{13}$ is alkyl or hydroxyl alkyl with 1 to 4 carbon atoms group and n is a number between 1 to 6, preferably 2 or 3. The preferred compound according to the above chemical structure is cetyl-PG-hydroxyethylpalmitamide. Concentration of ceramide type of compounds ranges from 0.01% to 2%, preferably 0.01% to 1% by weight calculated to the total of the composition.

The composition may further comprise ubiquinone of the formula:

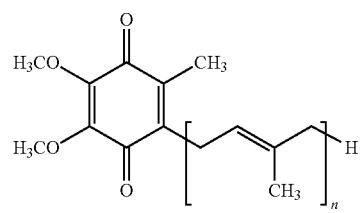

wherein n is a number from 1 to 10. The concentration of ubiquinone can vary between 0.001% and 10% by weight, calculated to the total of the composition.

The composition may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1% to 10%, preferably 0.5% to 7.5% and more preferably 0.2% to 5% and most preferably 1% to 5% by weight, calculated to the total of the composition.

The compositions may further comprise one or more polyol, preferably at a concentration in the range of 0.01% to 5%, preferably 0.1% to 3% and more preferably 0.2% to 2.5% and most preferably 0.25% to 2% by weight calculated to the total of the composition. Suitable ones are propylene glycol, dipropylene glycol, glycerine, panthenol and its derivatives.

The composition may comprise vitamins and/or their derivatives such as vitamins A, B group, C, D group, E group, and K. It may further comprise antioxidants such as green tea extract, emblica extract, rosemary extract, and ginkgo extract.

The composition may further comprise proteins or hydrolyzed proteins such as keratin, elastin, collagen, or the ones generated from wheat, barley, *quinoa*, rye, rice, milk, amaranth, hazelnut, corn, soybean, avocado, brazil nut, casein, cottonseed, egg, honey, jojoba, oat, potato, royal jelly, sesame, silk, sweet almond, whey, and yeast. Proteins or protein hydrolyzates are comprised at a concentration in the range from 0.01% to 5%, preferably 0.1% to 3% and more preferably 0.2% to 2.5% and most preferably 0.25% to 2% by weight, calculated to the total of the composition.

In another embodiment of the present invention the composition comprise one or more hair direct dyes. Suitable ones are cationic, anionic and nitro dyes. Plant dyes are also suitable for the compositions of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, and HC Blue 17.

Suitable nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder.

The composition may comprise one or more hair direct dye at a total concentration of 0.01% to 10%, preferably 0.05% to 7.5% and more preferably 0.1% to 5% by weight calculated to the total of the composition. The composition can also comprise a mixture of several direct dyes, i.e., an anionic, a cationic and/or nonionic ones. In such a case the dyes may be mixed at any ratio with each other.

The composition of the present invention has the viscosity in the range from 100,000 mPas to 1,000,000 mPas, preferably from 100,000 mPas to 750,000 mPas, more preferably from 150,000 mPas to 500,000 mPas, measured with a Brookfield viscosimeter at 20° C. with an appropriate spindle.

The composition may further comprise any known preservatives if necessary.

The following examples are to illustrate the invention, but not to limit it.

Example 1

| Ingredient | Inventive (w/w) | Comparative (w/w) |
|---|---|---|
| Cetearyl alcohol | 4.0% | 4.0% |
| Petroleum jelly | 20.0% | 20.0% |
| Bis-diglyceryl polyacyladipate-2 | 19.0% | 19.0% |
| Light mineral oil | 7.0% | 7.0% |
| VP/VA copolymer | 5.0% | 5.0% |
| PVP [30 kDa] | 3.0% | 3.0% |
| Ceteareth-25 | 2.3% | 2.3% |
| PEG-40 castor oil | 1.4% | 1.9% |
| Potassium cetyl phosphate | 0.5% | — |
| Water | ad 100% | ad 100% |

The performance of the compositions was investigated on human mannequins in a half-side comparison test. Coarse hair was received by pre-bleaching the hair with a commercial bleach available under the Goldwell SilkLift Control brand. Bleaching was conducted for 40 min at room temperature, then the hair was washed with a shampoo available under the brand Goldwell Dualsenses Deep Cleansing Shampoo. The hair was blow dried prior to use. 2 g of each composition (inventive, comparative) was applied onto the mannequin's hair. 10 mannequins were used for the test and the evaluation was independently performed by 10 expert panelists.

| Criterion: Inventive vs. Comparative | Better | Comparable | Worse |
|---|---|---|---|
| Application on hair | 7 | 3 | 0 |
| Distribution | 6 | 4 | 0 |
| Manageability | 6 | 4 | 0 |
| Softness | 8 | 2 | 0 |

The results clearly demonstrated that the inventive composition was much easier to apply to coarse hair and easier to distribute in the hair, while also conferring coarse hair a superior manageability and softness. Furthermore, the hair was visually evaluated by the expert panelists and it was possible to style the hair in various ways as was confirmed by the panelists.

The inventive and comparative compositions were measured for their viscosity with a Brookfield viscometer at 20° C. at 10 rpm (measurable range: 300-430 Pas). An appropriate spindle was selected. The compositions were measured three times upon preparation and three times upon storage for 6 months. For the storage stability test, each composition was filled into glass vials which were sealed with an air-tight cap. Standardized storage conditions were selected at 5° C., 25° C., and 40° C. The reported values below represent averages of three measurements at room temperature.

| Inventive | 5° C. | 25° C. | 40° C. |
|---|---|---|---|
| Upon preparation [mPas] | 345.000 | 345.000 | 345.000 |
| Upon 6 months of storage [mPas] | 352.000 | 369.000 | 421.000 |
| Increase [%] | 2.03 | 6.96 | 22.03 |

| Comparative | 5° C. | 25° C. | 40° C. |
|---|---|---|---|
| Upon preparation | 310.000 | 310.000 | 310.000 |
| Upon 6 months of storage | 356.000 | 372.000 | Phase separation visually detectable |
| Increase [%] | 14.84 | 20.00 | n.a. |

The viscosity results clearly showed that the comparative composition exhibited a phase separation upon 40° C. storage for 6 months. Although there was a trend of viscosity increase observed for the inventive composition, the aforementioned composition remained fully stable. At the lower temperatures, 5° C. and 25° C., the viscosity increase of the comparative composition was much higher compared to the inventive composition pointing to lower overall stability. In summary, the inventive composition was much more stable upon storage compared to the comparative composition.

The following examples are within the scope of the present invention.

Example 2

| Ingredient | Inventive (w/w) |
|---|---|
| Cetearyl alcohol | 15.0% |
| Light mineral oil | 14.0% |
| Bis-diglyceryl polyacyladipate-2 | 19.0% |
| VP/VA copolymer | 5.0% |
| PVP [90 kDa] | 3.0% |
| Ceteareth-25 | 2.3% |
| PEG-40 castor oil | 1.4% |
| Tetradecyl dihydrogen phosphate | 0.6% |
| Water | ad 100% |

2 g of the composition was applied to human hair and the hair exhibited good manageability and softness.

Example 3

| Ingredient | Inventive (w/w) |
|---|---|
| Cetearyl alcohol | 12.0% |
| Light mineral oil | 15.0% |
| Bis-diglyceryl polyacyladipate-1 | 19.0% |
| VP/VA copolymer | 5.0% |
| PVP [30 kDa] | 3.0% |
| Ceteareth-25 | 2.3% |
| PEG-40 castor oil | 1.4% |
| Dioctyl hydrogen phosphate | 0.8% |
| Water | ad 100% |

2 g of the composition was applied to human hair and the hair exhibited good manageability and softness.

Example 4

| Ingredient | Inventive (w/w) |
|---|---|
| Isopropyl pamitate | 4.0% |
| Hydrogenated castor oil | 24.0% |
| Bees wax | 20.0% |
| VP/VA copolymer | 5.0% |
| PVP [30 kDa] | 3.0% |
| Ceteareth-25 | 2.3% |
| PEG-40 castor oil | 1.4% |
| Sodium octyl phosphate | 0.8% |
| Water | Ad 100% |

2 g of the composition was applied to human hair and the hair exhibited good manageability and softness.

Example 5

| Ingredient | Inventive (w/w) |
|---|---|
| Oleic acid | 6.0% |
| Cetyl palmitate | 22.0% |
| Carnauba wax | 18.0% |
| VP/VA copolymer | 5.0% |
| PVP [30 kDa] | 3.0% |
| Ceteareth-25 | 2.3% |
| PEG-40 castor oil | 1.4% |
| Dodecyl dihydrogen phosphate | 0.4% |
| Water | Ad 100% |

2 g of the composition was applied to human hair and the hair exhibited good manageability and softness.

Example 6

| Ingredient | Inventive (w/w) |
|---|---|
| Olive oil | 4.0% |
| Mineral oil | 10.0% |
| Stearyl alcohol | 25.0% |
| VP/VA copolymer | 5.0% |
| PVP [30 kDa] | 3.0% |
| Ceteareth-25 | 2.3% |
| PEG-40 castor oil | 1.4% |
| Potassium cetyl phosphate | 0.5% |
| Water | Ad 100% |

2 g of the composition was applied to human hair and the hair exhibited good manageability and softness.

Example 7

| Ingredient | Inventive (w/w) |
|---|---|
| Olive oil | 4.0% |
| Mineral oil | 10.0% |
| Myristic acid | 20.0% |
| VP/VA copolymer | 5.0% |
| PVP [30 kDa] | 3.0% |
| Ceteareth-25 | 2.3% |
| PEG-40 castor oil | 1.4% |
| Potassium cetyl phosphate | 0.5% |

-continued

| Ingredient | Inventive (w/w) |
|---|---|
| Ubiquinone 10 | 0.25% |
| Hydrolyzed milk proteins | 1.0% |
| Cetyl-PG-hydroxyethylpalmitamide | 0.2% |
| Water | Ad 100% |

2 g of the composition was applied to human hair and the hair exhibited good manageability and softness.

What is claimed is:

1. An aqueous composition for styling hair, consisting of:
   a) one or more fatty substances at a concentration of 1 to 25% by weight, calculated to the total of the composition, selected from the group consisting of castor oil, coconut oil, corn oil, cottonseed oil, olive oil, palm kernel oil, peanut oil, rapeseed oil, sunflower oil, safflower oil, sesame oil, soybean oil, almond oil, cashew oil, hazelnut oil, jojoba oil, macadamia oil, pecan oil, pine nut oil, pistachio oil, walnut oil, grapefruit seed oil, lemon oil, orange oil, pumpkin seed oil, flaxseed oil, apricot kernel oil, argan oil, avocado oil, babassu oil, grape seed oil, mustard oil, poppyseed oil, prune kernel oil, rice bran oil, wheat germ oil, oleyl alcohol, 2-octyldodecyl alcohol, isostearyl alcohol, ricinoleic acid, caprylic acid, arachidonic acid, oleic acid, and linoleic acid, isopropyl palmitate, light mineral oils and their mixtures,
   b) one or more waxes at a concentration of 25-60% by weight, calculated to the total of the composition, selected from the group consisting of beeswax, lanolin wax, carnauba wax, candelilla wax, ouricury wax, rice bran wax, berry wax, shellac wax, orange wax, lemon wax, microcrystalline waxes, petroleum jelly, bis-diglyceryl polyacyladipate-1, bis-diglyceryl polyacyladipate-2, octyl stearate, myristyl myristate, cetyl palmitate, octyl palimitate, lauryl palmitate, cetyl alcohol, stearyl alcohol, cetearyl alcohol, lauric acid, myristic acid, palmitic acid, stearic acid, behenic acid, and their mixtures,
   c) one or more anionic surfactants and/or their salts according to the general structure

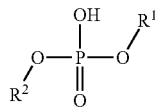

wherein $R^1$ is a linear alkyl chain with $C_6$ to $C_{22}$, and $R^2$ is selected from H or linear alkyl chain with $C_6$ to $C_{12}$ with the proviso that if $R^2$ is H then $R^1$ is selected from $C_{12}$ to $C_{22}$, and
   d) one or more styling polymers at a concentration of 1 to 20% by weight, calculated to the total of the composition,
   e) optionally one or more of the ingredients selected from the group consisting of non-ionic surfactants, ceramide compounds, lipids, ubiquionones, organic solvents, polyols, vitamins and/or their derivatives, proteins or hydrolysed proteins, direct hair dyes, and preservatives, and f) water,
   wherein the composition has a viscosity in the range from 100,000 mPas to 1,000,000 mPas, measured with a Brookfield viscosimeter at 20° C. with an appropriate spindle.

2. The composition according to claim 1, wherein the weight ratio (b):(a) of (b) the total waxes to (a) total fatty substances is in the range from 1 to 10, wherein the composition is an oil in water emulsion.

3. The composition according to claim 2, wherein the ratio (b):(a) is 1 to 5.

4. The composition according to claim 3, wherein the ratio (b):(a) is 1 to 3.

5. The composition according to claim 1, wherein the anionic surfactant is cetyl phosphate and/or its salts.

6. The composition according to claim 1, wherein the one or more styling polymers is selected from anionic, cationic, amphoteric, and non-ionic polymers.

7. The composition according claim 6, wherein the non-ionic styling polymer is a homopolymer of vinylpyrrolidone.

8. The composition according to claim 1, wherein the total concentration of anionic surfactants and/or their salts is in the range from 0.1% to 10%, calculated to the total of the composition.

9. The composition according to claim 1, wherein component e) is present and is one or more non-ionic surfactants selected from the group consisting of an ester of ethylene oxide, an ether of ethylene oxide, a fatty acid, and a fatty alcohol.

10. The composition according to claim 9, wherein the weight ratio of total anionic to total non-ionic surfactant is from 0.1 to 20.

11. The composition according to claim 1, wherein component e) is present and is selected from the group consisting of ceramides, lipids, ubiquionone, organic solvents, vitamins, proteins or hydrolysed proteins and preservatives.

12. The composition according to claim 1, wherein component e) is present and is a hair direct dye.

13. A system comprising a kit comprising the components of the composition according to claim 1, either together or in groups of one, two or three components, and a shampoo and/or blow dryer.

14. The aqueous composition of claim 1, wherein the one or more fatty substances is from the group consisting of light mineral oils, castor oil, isopropyl pamlitate, oleic acid, olive oil.

15. The aqueous composition of claim 1, wherein the one or more waxes is selected from the group consisting cetearyl alcohol, stearyl alcohol, petroleum jelly, bis-diglyceryl polyacyladipate-1, bis-diglyceryl polyacyladipate-2, beeswax, cetyl pamitate, carnauba wax, myristic acid, and/or their mixtures.

* * * * *